United States Patent [19]

Selega et al.

[11] 4,237,112

[45] Dec. 2, 1980

[54] MEDICATED HAIR AND SCALP CONDITIONER

[75] Inventors: Zbigniew J. Selega, Mt. Prospect; Ezzat N. Khalil, Oak Park; Gloria M. McKavanagh, Chicago, all of Ill.

[73] Assignee: Johnson Products Co., Inc., Chicago, Ill.

[21] Appl. No.: 42,720

[22] Filed: May 25, 1979

[51] Int. Cl.$^3$ .................. A61K 7/06; A61K 33/04
[52] U.S. Cl. .................. 424/70; 424/162; 424/164; 424/168; 424/357
[58] Field of Search .................. 424/164, 162, 70, 168

[56] References Cited

U.S. PATENT DOCUMENTS

| | | | |
|---|---|---|---|
| 3,265,571 | 8/1966 | Krezanoski | 424/162 |
| 4,087,555 | 5/1978 | Barnett et al. | 424/362 |
| 4,155,994 | 5/1979 | Merianos | 424/70 |

FOREIGN PATENT DOCUMENTS

| | | | |
|---|---|---|---|
| 880282 | 9/1971 | Canada | 424/164 |
| 1050024 | 2/1959 | Fed. Rep. of Germany | 424/162 |
| 2707537 | 8/1977 | Fed. Rep. of Germany | 424/164 |
| 836799 | 10/1938 | France | 424/168 |
| 1331907 | 6/1963 | France | 424/168 |
| 413895 | 7/1946 | Italy | 424/162 |
| 46-13276 | 4/1971 | Japan | 424/319 |
| 821726 | 10/1959 | United Kingdom | 424/62 |

OTHER PUBLICATIONS

CTFA Cosmetic Ingredient Dictionary, 2nd edition, 1977, pp. 279 (Exhibit N), & 314 (Exhibit O), 360 (Exhibit D).
Pigments and Chemicals Division-NL Industries, Inc. Exhibits (A) to (C), (E) to (I), (K) to (N).
Goodman, Cosmetic Dermatology, 1937, pp. 234-244.

*Primary Examiner*—Dale R. Ore
*Attorney, Agent, or Firm*—Dressler, Goldsmith, Shore, Sutker & Milnamow, Ltd.

[57] ABSTRACT

An anhydrous medicated hair and scalp conditioner comprising sulfur as a medicament, petrolatum, mineral wax, dispersant and about 1 to about 30 weight percent organically modified hectorite clay gellant is produced having a one phase appearance. The medicated hair and scalp conditioner is prepared by admixing the gellant in petrolatum heated to about 80°-85° C., followed by melting and admixture therein of the mineral wax at the same temperature. Sulfur is dispersed in the dispersant in a separate container and the resultant dispersion then added to the previous admixture at a temperature of about 75°-80° C. The resulting composition is then agitated for about 30 minutes while allowing the temperature to cool to about 70° C., after which the composition is collected.

4 Claims, No Drawings

MEDICATED HAIR AND SCALP CONDITIONER

TECHNICAL FIELD

This invention relates to hair and scalp treatment compositions.

BACKGROUND ART

The use of sulfur-containing products for the treatment of the hair and scalp to combat seborrhea dates at least to the first decade of the twentieth century and has continued through the present. In these sulfur-containing preparations, the sulfur generally is colloidal, and has been suspended in aqueous, hydrophilic ointments as well as anhydrous, hydrophobic compositions.

One problem which has remained throughout the long history of the use of sulfur-containing compositions is the fact that sulfur is not soluble in the composition, and even in colloidal size, particles tend to form a separate and distinct phase in the compositions. This separate and distinct phase can take the form of isolated sulfur particles or crystals which are visible throughout the composition and also as a precipitate which settles at or near the bottom of such compositions. The latter situation is particularly disadvantageous because it goes beyond appearance and affects the effectiveness of the product for its intended function. Even if the product is restirred by hand before use, the distribution of sulfur therein is frequently non-uniform, resulting in a non-uniform application of sulfur on the hair or scalp.

Efforts to solve the problem of having two phases in such sulfur-containing compositions have generally failed, with the result being that compositions are made and sold having a cosmetically unattractive two-phase appearance. One attempt to solve the problem associated with two-phase systems has been the use of colloidal sulfur in conjunction with a colloidal co-suspending agent such as gum arabic (acacia). Nevertheless, even though preparations containing colloidal sulfur and acacia disperse readily in water to give milky fluids, on standing such dispersions generally form a precipitate so the dispersions should be freshly prepared for use.

BRIEF SUMMARY OF THE INVENTION

This invention relates to an anhydrous medicated hair and scalp conditioning composition comprising sulfur as a medicament, petrolatum, mineral wax, dispersant, and an organically modified hectorite clay gellant, which clay gellant is present in the composition at about 1 to about 30 percent of the total composition. The inclusion of the hectorite gellant causes the composition to have and retain a one phase appearance.

The compositions of this invention may be prepared by heating petrolatum to a temperature of about 80° to about 85° C. with agitation. The hectorite clay gellant is then admixed therein while maintaining the temperature and agitation. The temperature and agitation are maintained until the gellant is substantially dispersed within the petrolatum and the resulting admixture is substantially lump-free. The hardening wax is then admixed into the lump-free admixture, while maintaining the temperature and agitation until the wax is melted and a substantially homogeneous admixture is formed. In a separate container, sulfur is sifted into the dispersant with agitation to form a dispersion of sulfur therein. The sulfur-containing dispersion is then admixed with agitation into the homogeneous admixture whose temperature has been lowered to about 75° to 80° C. The resulting compositions is then agitated for about 30 minutes starting at a temperature of about 75° C. to 80° C. and ending at a temperature of about 70° C., at which the completed product is collected, and cooled.

DISCLOSURE OF THE INVENTION

It has now been found that a one phase, non-settling anhydrous medicated hair and scalp conditioning composition may be prepared containing sulfur as a useful medicament. In these compositions, the sulfur does not form an apparent second or separate phase and does not settle out on aging, nor when the composition is heated to a liquid state and centrifuged. This startling result is caused, or brought about by the incorporation of about 1 to about 30 weight percent of organically modified hectorite clay gellant into a sulfur-containing hair and scalp conditioning composition.

Organically modified hectorite clay gellants are known to give thixotropic cosmetic products such as hair grooming preparations. These gellants are also known to be particularly useful for pigment suspension in products such as eye and face makeups and lip products. It is additionally known that compositions containing quaternium-18 hectorite, mineral oil and alcohol are chemically compatible with sulfur incorporated therein with the use of small amounts of liquid petrolatum as a levigating agent. However, the potent dispersing effect of these materials on sulfur to form and retain the apparent one phase system of the present invention has not heretofore been known and is not suggested by the art.

It is presently not known whether the organically modified hectorite clay gellants dissolve or disperse the sulfur in the products of this invention. Regardless of whether a solution or dispersion is formed, the appearance of the products of this invention is quite startling in comparison to the sulfur-containing products presently in the market place. The products of this invention are translucent gels having only one apparent phase, while the commercially available products have easily visible particles suspended therein or collected on jar bottoms.

Sulfur is soluble in lanolin at 45° C., and one of the gellants (described hereinbelow) contains some lanolin oil (dewaxed lanolin). Whether there is enough lanolin present to cause dissolution or dispersion of the sulfur is unknown. Since it has also been found that all of the hereinbelow discussed hectorite gellants disperse or dissolve the sulfur to approximately the same degree, it is not believed that the lanolin present in the one gellant plays a significant role in the sulfur solution or dispersion observed in this invention.

Organically modified hectorite clay gellants are sold by N.L. Industries, Inc. under the trademark name "Bentone." The hectorite gellants are comprised of hectorite modified with a quaternary nitrogen-containing compound and then further modified by the incorporation of propylene carbonate and various organic liquids. The compositions of most of the commercially available hectorite gellants are listed in the *CTFA Cosmetic Ingredient Dictionary*, 2nd ed., published by the Cosmetic, Toiletry and Fragrance Association, Inc. at page 360.

Specific, commercially available, useful gellants as listed above include: Bentone Gel CAO, comprised of propylene carbonate, castor oil and stearalkonium hectorite; Bentone Gel IPM, comprised of propylene carbonate, isopropyl myristate and stearalkonium hectorite; Bentone Gel Lantrol, comprised of propylene carbonate, a mixture of lanolin oil (dewaxed lanolin) and isopropyl palmitate, and stearalkonium hectorite; Bentone Gel MIO, comprised of propylene carbonate, mineral oil and quaternium-18 (dimethyl-di- (hydrogenated follow) ammonium chloride hectorite; and Bentone Gel M20, comprised of propylene carbonate, a mixture of propylene glycol dicaprylate and propylene glycol dicaprate, and stearalkonium hectorite. In addition, Bentone Gel IPP, comprised of propylene carbonate, isopropyl palmitate and stearalkonium hectorite may be used. This material, while commercially available is not listed in the above *CTFA Cosmetic Ingredient Dictionary*. The above hectorite gellants are not only individually useful in the compositions of this invention, but may be interchanged, one for the other, in a given composition, and may be mixed together in a single composition.

The modified hectorite gellants may be present in the composition of the instant invention from about 1 to about 30 weight percent of the total composition. Below about 1 percent of the total composition, too little sulfur is dissolved or dispersed to give the product its desired one phase appearance. Above about 30 weight percent, use of the gellant becomes wasteful.

Sulfur is present in the compositions of this invention at about 0.15 to 2.25 weight percent of the total composition. The sulfur used should be a pharmaceutical or cosmetic grade and have finely divided or colloidal size particles so that at least 95 percent by weight of the sulfur will pass through a U.S. No. 200 sieve.

Medicaments other than sulfur are additionally useful herein. It has been found that incorporation of 3,5-dimethyl-4-chlorophenol which is a known anti-dandruff agent and also offers protection against both Gram-positive and Gram-negative bacteria, is also advantageous. The 3,5-dimethyl-4-chlorophenol, also known as para-chloro-meta-xylenol, has been found to be useful at about 0.05 to about 0.35 weight percent of the total composition.

The dispersants of the instant invention are principally chosen from the difatty acid esters of polyethylene oxide. The polyethylene oxide portion of these molecules has the molecular formula $H(OCH_2CH_2)_nOH$, wherein n is the average number of ethylene oxide units. Typically, n has an average value of about 4 to about 150, but those materials having an average n value of about 6 to about 12 ethylene oxide units per molecule are preferred. Dispersants having an n value of 8 are particularly preferred.

The fatty acid portion of the dispersant molecules may be selected from the group of fatty acids including lauric acid, oleic acid, stearic acid, tall oil acid and the like. Preferably, the dispersants are comprised of diesters of lauric acid. Thus, the preferred dispersant is the dilauric acid ester of a polyethylene oxide having an average of 8 ethylene oxide units and may be named polyoxyethylene (8) dilaurate. It is named PEG-8 dilaurate in the above cited *CTFA Cosmetic Ingredient Dictionary* at p. 207.

The dispersant is present in the compositions of this invention at at least 0.5 weight percent, with the upper limit being determined by the remaining components of the composition. Thus, the dispersant also functions as a diluent.

The principal component by weight of the compositions of this invention is petrolatum. Petrolatum may be present at about 50 to about 94 weight percent of the total composition. Petrolatum is commercially available in several colors, ranging from white (colorless) to dark brown, having melting point ranges from 46°–57° C. through 71°–77° C. and having viscosities which range from about 8.7–14.2 to about 11.6–18.0 cst at 100° C. Preferably, white petrolatum having a melting point range of about 54°–60° C. and a viscosity range of about 10.2–15.5 cst at 100° C. is used.

Ozokerite wax is included in the composition of this invention to raise the melting point and hardness thereof so that the composition has a room temperature consistency similar to that of a heavy grease. Ozokerite waxes are bituminous hydrocarbon materials derived from mineral or petroleum sources. They typically have long fibers, unlike the structure of paraffins and microcrystaline waxes. These materials are available in white and yellow colors with melting point ranges from about 145°–155° F. through about 188°–198° F. These waxes are also characterized by a penetration test at 77° F. as is customary for the wax industry and these materials have penetration values ranging from about 4 to about 25. Preferably, a white ozokerite wax having a melting point range of 164°–174° F. and a penetration value of 8 is used. The ozokerite wax may be present at about 0.5 to about 5 weight percent of the total composition.

The amounts of petrolatum, hectorite gellant, ozokerite wax and dispersant may be "played" against each other to control the consistency and the "melting point" of the final composition as is known in the art. What may be termed "melting point" is measured by a drop point temperatutre test discussed hereinbelow.

The dropping or drop point is a standard test in the grease industry. It may be defined as the temperature at which drops of liquid grease fall from a tube of grease surrounding a thermometer with the tube having a standard orifice at the bottom. The drop point is measured when the first drop of sample hits the bottom of the test device.

Drop point test devices are available commercially. An instrument manufactured by Stanhope-Seta, Ltd. of Chertsey, Surrey, England has been used for the determinations hereinreported.

Drop points of about 46° to about 54° C. are preferred for the compositions of this invention. Example 2–8 (hereinbelow) demonstrate the effect on the drop point of identical amounts of different hectorite clay gellants used in compositions whose other components, components amounts and manufacturing procedures are substantially identical.

In addition to the above-mentioned ingredients, other ingredients such as dyes, menthol, fragrances and the like may also be included in the compositions of this invention for their own cosmetic or other effects.

The compositions of this invention may be prepared by shifting colloidal sulfur into the dispersant. The admixture is mixed for at least about 30 minutes, and mixing is continued until the entire composition is formulated. Sulfur is sifted into the composition to avoid agglomeration or lump formation.

Petrolatum is added to a separate, heatable container and heated to about 80° to about 85° C.. The hectorite gellant is added in increments thereto with rapid agitation. Rapid agitation is continued until the gellant is substantially completely dispersed and the admixture is substantially lump-free. The ozokerite wax is then added to the petrolatum-gellant admixture, while agitation and maintenance of a temperature of about 80° are continued. This resultant admixture is mixed thoroughly until substantially all the wax is melted and a substantially homogeneous admixture is formed. This generally requires about 30 minutes of mixing.

With the temperature of the above resultant admixture at about 75° to 80° C., the above prepared dispersed sulfur admixture is admixed therein to form a new admixture. This new admixture is then mixed at a temperature of about 75° to 80° C. for an additional 30 minutes during which time the composition becomes almost clear. During the agitation, the temperature of the composition is allowed to cool slightly to about 70° C. After the 30 minutes of mixing and a temperature of about 70° C. has been obtained, the composition may be discharged for use and allowed to cool. On cooling, the composition becomes a translucent gel.

When additional medicaments, such as the anti-dandruff agent, 3,5-dimethyl-4-chlorophenol, are used, the additional medicament is added to the dispersant and dissolved therein prior to the sulfur addition. When dyes are used they too are dissolved in the dispersant prior to the addition of sulfur. When fragrance and menthol are used in a composition, these materials are added separately after the composition has cooled to about 70° C. and the materials are added at about that temperature. Thorough mixing (about 15 minutes) follows each separate addition.

BEST MODES FOR CARRYING OUT THE INVENTION

EXAMPLES 1 and 2.

| Medicated Hair and Scalp Conditioners (Weight Percent) | | |
|---|---|---|
| Components | 1 | 2 |
| Petrolatum | 93.045 | 50.00 |
| Modified Hectorite Clay Gellant (Note 2) | 1.00 | 30.00 |
| Ozokerite Wax (Note 3) | 5.00 | 0.50 |
| Dispersant (Note 4) | 0.50 | 13.15 |
| Anti-dandruff Agent (Note 5) | 0.05 | 0.35 |
| Sulfur (as sulfur) (Note 6) | 0.15 | 2.25 |
| Menthol | 0.10 | 2.00 |
| Fragrance | 0.10 | 1.00 |
| Dyes | 0.005 | 0.005 |
| Drop Point, °C. | 52.25 | 46.0 |

(Note 1) A white petrolatum having a melting point of 54–60° C. and a viscosity of 10.2–15.5 cst at 100° C. was used.
(Note 2) A modified hectorite clay gellant comprised of propylene carbonate, a mixture of lanolin oil and isopropyl myristate, and stearalkonium hectorite was used. It is commercially available from N. L. Industries, Inc. under the tradename Bentone Gel Lantrol.
(Note 3) A white ozokerite wax having a melting point of 164–174° F. and penetration at 77° F. of 8 was used.
(Note 4) A dispersant comprised of polyoxyethylene (8) dilaurate was used.
(Note 5) An anti-dandruff agent comprised of 3,5-dimethyl-4-chlorophenol was used.
(Note 6) A dried colloidal sulfur powder consisting of 75% sulfur, and acacia, having 2% maximum ash, 3% maximum water and a minimum 95% of which will pass through a U.S. No. 200 sieve was used. Because the sulfur used was not pure sulfur, the numbers in the tables herein do not add up to 100%.

Note 6. A dried colloidal sulfur powder consisting of 75% sulfur, and acacia, having 2% maximum ash, 3% maximum water and a minimum 95% of which will pass through a U.S. No. 200 sieve was used. Because the sulfur used was not pure sulfur, the numbers in the tables herein do not add up to 100%.

The anti-dandruff agent was dissolved in the dispersant at ambient temperature. Dyes were then added with mixing until they dissolved. The sulfur was sifted into the solution and the resulting dispersion mixed after addition for 30 minutes to form component mixture A. Agitation of component mixture A was continued until addition to the below-described component mixture B.

Petrolatum was added to a heatable container and heated and agitated until a temperature of about 80°–85° C. was reached, at which time heating was discontinued. The modified hectorite gellant was added in increments and with rapid agitation. This petrolatum-hectorite admixture was mixed until the hectorite was substantially completely dispersed and the composition was substantially homogeneous and lump-free. Ozokerite wax was then added at an admixture temperature of 80° C. to form a new wax-containing admixture. The new wax-containing admixture was stirred for 30 minutes until substantially all of the wax was melted, and a substantially homogeneous admixture was formed. This admixture is component mixture B.

Component mixture A was added to B with mixing while maintaining a temperature of 75°–80° C. The resulting composition was stirred for 30 minutes and allowed to cool during this time period to 70° C. At the end of the 30 minute stirring period, menthol was added with maintenance of the 70° C. temperature, followed by an additional agitation period of 15 minutes. The fragrance was then added with maintenance of the 70° C. temperature followed by another 15 minutes of agitation. The thereby resulting product was then discharged into containers for use, and cooled.

Both of the above medicated hair and scalp conditioners exhibited only one apparent phase and no unsightly particulate matter could be seen on aging.

EXAMPLES 3–8

| | Medicated Hair and Scalp Conditioners (Weight Percent) | | | | | |
|---|---|---|---|---|---|---|
| | Examples | | | | | |
| Components | 3 | 4 | 5 | 6 | 7 | 8 |
| Petrolatum (Note 1, above) | 80.895 | 80.895 | 80.895 | 80.895 | 80.895 | 80.895 |
| Modified Hectorite Clay Gellant | 10.00 (Note 2, above) | 10.00 (Note 7) | 10.00 (Note 8) | 10.00 (Note 9) | 10.00 (Note 10) | 10.00 (Note 11) |
| Ozokerite Wax (Note 3, above) | 2.00 | 2.00 | 2.00 | 2.00 | 2.00 | 2.00 |
| Dispersant (Note 4, above) | 5.00 | 5.00 | 5.00 | 5.00 | 5.00 | 5.00 |
| Anti-dandruff Agent (Note 5, above) | 0.20 | 0.20 | 0.20 | 0.20 | 0.20 | 0.20 |
| Sulfur (active) (Note 6, above) | 0.75 | 0.75 | 0.75 | 0.75 | 0.75 | 0.75 |
| Menthol | 0.50 | 0.50 | 0.50 | 0.50 | 0.50 | 0.50 |
| Fragrance | 0.40 | 0.40 | 0.40 | 0.40 | 0.40 | 0.40 |
| Dyes | 0.005 | 0.005 | 0.005 | 0.005 | 0.005 | 0.005 |
| Drop | | | | | | |

| Components | Medicated Hair and Scalp Conditioners (Weight Percent) Examples | | | | | |
|---|---|---|---|---|---|---|
| | 3 | 4 | 5 | 6 | 7 | 8 |
| Point, °C. | 47.75 | 47.38 | 46.13 | 48.25 | 46.38 | 53.5 |

(Note 7) A modified hectorite clay gellant comprised of propylene carbonate, mineral oil and quaternium-18 hectorite, commercially available from N. L. Industries, Inc. under the trademark name Bentone Gel MIO was used.
(Note 8) A modified hectorite clay gellant comprised of propylene carbonate, isopropyl myristate and stearalkonium hectorite, commercially available from N. L. Industries, Inc. under the trademark name Bentone Gel IPM was used.
(Note 9) A modified hectorite clay gellant comprised of propylene carbonate, isopropyl palmitate and stearalkonium hectorite, commercially available from N. L. Industries, Inc. under the trademark name Bentone Gel IPP was used.
(Note 10) A modified hectorite clay gellant comprised of propylene carbonate, a mixture of propylene glycol dicaprylate and propylene glycol dicaprate, and stearalkonium hectorite, commercially available from N. L. Industries, Inc. under the trademark name Bentone Gel M20 was used.
(Note 11) A modified hectorite clay gellant comprised of propylene carbonate, castor oil and stearalkonium hectorite, commercially available from N. L. Industries, Inc. under the trademark name Bentone Gel CAO was used.

The compositions of Examples 3-8 were prepared in a fashion similar to Examples 1-2 with some sight alterations. Thus, component mixture A was prepared as recited for Examples 1-2.

Petrolatum and the modified hectorite clay gellant were added to a heatable container, and heated and agitated until a temperature of about 60° C. was reached. Agitation and temperature maintenance were continued until the hectorite was substantially dispersed and the admixture was substantially lump-free. The ozokerite wax and menthol were then added and the temperature raised to about 80° C. Agitation at a temperature of about 80° C. was continued until the wax was substantially completely melted, and a substantially homogeneous admixture was formed. The latter agitation lasted for about 30 minutes. This admixture was component mixture B.

Component mixture A was added to component mixture B with mixing while maintaining a temperature of 75°-80° C. The resulting composition was stirred for 30 minutes and allowed to cool during this time period to 70° C. The fragrance was added with maintenance of the 70° C. temperature, at the end of the 30 minute stirring period, followed by another 15 minutes of agitation. The thereby resulting product was then discharged into containers for use, and cooled.

The procedure used in preparing Examples 1-2 has been found preferable to that used immediately above in that better retention of the menthol odor is obtained. It has also been found preferable to first melt the petrolatum, heat it to a temperature of about 80°-85° C. and then add the modified hectorite clay gellant incrementally while maintaining the 80°-85° C. temperature. The ozokerite wax is also preferably added to the admixture at about 80°-85° C.

All of the above medicated hair and scalp conditioners showed only one apparent phase. There was no unsightly particulate matter on aging (see Example 9 hereinbelow).

EXAMPLE 9

Settling Tests

Three separate tests were run on the medicated hair and scalp conditioners of this invention to determine whether settling or crystallization of the dispersed or dissolved sulfur would occur during heating after the product was made. In the first test, four 50 ml. centrifuge tubes were filled, two tubes each with a composition of this invention (Example 3) and a leading commercially available sulfur-containing hair and scalp conditioner. Equal weights of materials were used in the tubes, and the tubes were balanced after filling at room temperature. The four tubes were then covered with a paraffin film and placed in a beaker of water which was then heated to about 80° to about 85° C. The tubes were kept at this temperature until the material within the tubes was liquid or in a fluid state. By the time the products were liquified, the composition of Example 3 showed no precipitation while the commercially available product had a heavy white precipitate. The four tubes were then uncovered and centrifuged for 10 minutes. At the end of this time, the products had cooled and were firm. No precipitate was noted in the Example 3 composition, while the commercially available product had a heavy white precipitate.

In a second experiment a composition of this invention (Example 3) and the above-leading sulfur-containing hair and scalp conditioning product were placed in two separate aluminum dishes. The dishes were then heated to about 140° C. at which temperature the contents were water-thin. The liquids were then allowed to cool, and the films thereby produced were examined. The composition of Example 3 showed no particles or separation, but a continuous, apparently homogeneous film. The film produced by the commercially available sulfur-containing product showed a precipitate of sulfur or other particles.

In the third test, two preparations of the composition of Example 3 were placed in an oven at 70° C. for a period of 24 hours and examined every six hours for the presence of crystallization or sediment. No crystallization or sediment or settling of any kind was noted to the naked eye in either of the preparations at 6, 12, 18 or 24 hours.

This invention is defined by the claims which follow.

What is claimed:

1. A non-settling, anhydrous medicated hair and scalp conditioning composition consisting essentially of about 50 to about 94 weight percent petrolatum, about 0.5 to about 5 weight percent mineral wax, at least about 0.5 weight percent polyoxyethylene (8) dilaurate, about 0.15 to about 2.25 weight percent sulfur as a medicament and about 1 to about 30 weight percent of an organically modified hectorite clay gellant which consists of hectorite modified by propylene carbonate, stearalkonium chloride or dimethyl-di-(hydrogenated tallow) ammonium chloride and an organic liquid selected from the group consisting of mineral oil, castor oil, isopropyl myristate, isopropyl palmitate, a mixture of lanolin oil and isopropyl palmitate, and a mixture of propylene glycol dicaprylate and propylene glycol dicaprate, said composition having one apparent phase.

2. The composition according to claim 1 additionally comprising as a medicament therein about 0.05 to about 0.35 weight percent 4-chloro-3,5-di-methylphenol.

3. The method of making the composition according to claim 2 comprising the steps of:
heating said petrolatum to a temperature of about 80° to about 85° C. with agitation;
admixing therein said hectorite clay gellant while maintaining said temperature;
agitating said admixture at said temperature until said gellant is substantially dispersed and said admixture is substantially lump-free;
admixing said mineral wax to said lump-free admixture;

maintaining said temperature and agitation until said wax is melted, and a substantially homogeneous admixture is formed;

dissolving said 4-chloro-3,5-dimethylphenol in a separate container containing said polyoxyethylene (8) dilaurate to form a solution;

sifting said sulfur into said solution with agitation to form a dispersion of sulfur therein;

admixing and agitating said sulfur-containing dispersion into said homogeneous admixture to form said composition having a temperature of about 75° to about 80° C.;

agitating said composition for about 30 minutes, during which time said composition becomes translucent starting at a temperature of about 75° to about 80° C. and ending at a temperature of about 70° C.; and collecting said composition.

4. The method of making the composition according to claim 1 comprising the steps of:

heating said pretrolatum to a temperature of about 80° to about 85° C. with agitation;

admixing therein said hectorite clay gellant while maintaining said temperature;

agitating said admixture at said temperature until said gellant is substantially dispersed and said admixture is substantially lump-free;

admixing said mineral wax to said lump-free admixture;

maintaining said temperature and agitation until said wax is melted, and a substantially homogeneous admixture is formed;

sifting said sulfur with agitation into a separate container containing said polyoxyethylene (8) dilaurate to form a dispersion of sulfur therein;

admixing and agitating said sulfur-containing dispersion into said homogeneous admixture to form said composition having a temperature of about 75° to about 80° C.;

agitating said composition for about 30 minutes, during which time said composition becomes almost clear, starting at a temperature of about 75° to about 80° C. and ending at a temperature of about 70° C.; and collecting said composition.

* * * * *